United States Patent [19]

Pollak et al.

[11] 4,142,802

[45] Mar. 6, 1979

[54] METHOD AND APPARATUS FOR MEASURING VARIATIONS IN COMPOSITION IN BINARY AND TERNARY SEMICONDUCTORS UTILIZING ELECTROLYTE ELECTROREFLECTANCE

[75] Inventors: Fred H. Pollak, New York, N.Y.; Paul M. Raccah, Chicago, Ill.

[73] Assignee: Yeshiva University, New York, N.Y.

[21] Appl. No.: 855,831

[22] Filed: Nov. 30, 1977

[51] Int. Cl.² .......................... G01J 3/42; G01N 21/48
[52] U.S. Cl. ...................................... 356/319; 356/445
[58] Field of Search .............. 356/74, 96, 97, 209-212

[56] References Cited

U.S. PATENT DOCUMENTS 3,850,508  11/1974  Sittig et al. ........................... 356/209

OTHER PUBLICATIONS

Shaklee et al., *Physical Review Letters*, vol. 15, No. 23, Dec. 6, 1965, pp. 883-885.
Feinleib, *Physical Review Letters*, vol. 16, No. 26, Jun. 27, 1966, pp. 1200-1202.
Cardona et al., *Physical Review*, vol. 154, No. 3, Feb. 15, 1967, pp. 696-720.
Moritani et al., *Journal of the Physical Society of Japan*, vol. 34, No. 1, Jan. 1973, pp. 79-88.

*Primary Examiner*—F. L. Evans
*Attorney, Agent, or Firm*—Gottlieb, Rackman & Reisman

[57] ABSTRACT

There is disclosed an apparatus and method for measuring the variations in composition across the surface of binary and ternary alloy semiconductors utilizing electrolyte electroreflectance. The technique is non-destructive, can readily be employed under atmospheric conditions at room temperature, and is sensitive enough to determine changes of composition of about 1% with a spatial resolution of about $100\mu$. The procedure is very useful for the selection of crystals for detector arrays, solid states lasers, or electronic devices. It can also be utilized as a convenient tool for evaluating material grown either in bulk form or epitaxial layers, thus providing feedback for the adjustment of crystal growth parameters. The apparatus includes a mechanism for stepping the semiconductor being investigated in two dimensions while performing electroreflectance measurements; the measurement results can then be plotted on contour maps.

10 Claims, 5 Drawing Figures

FIG. 4
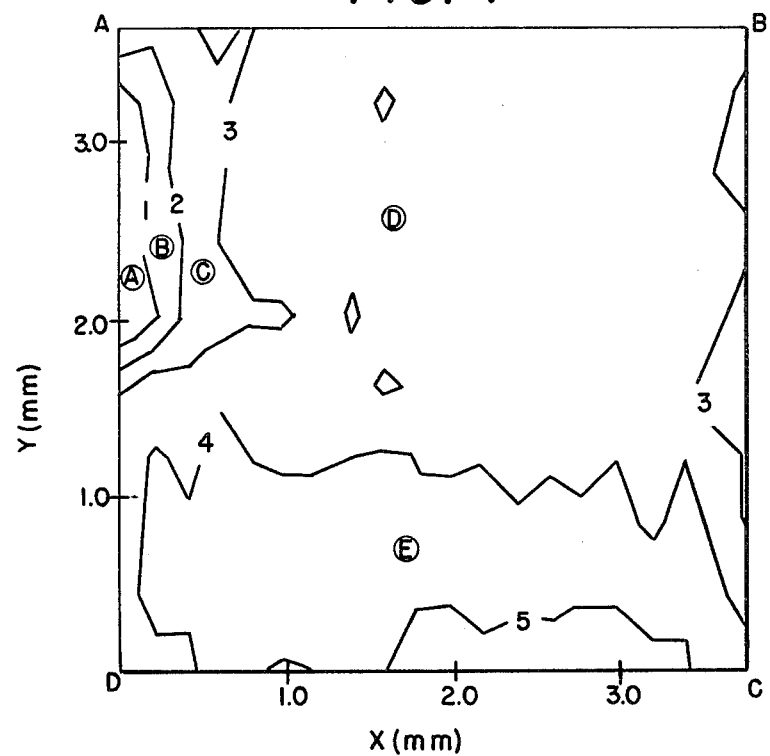
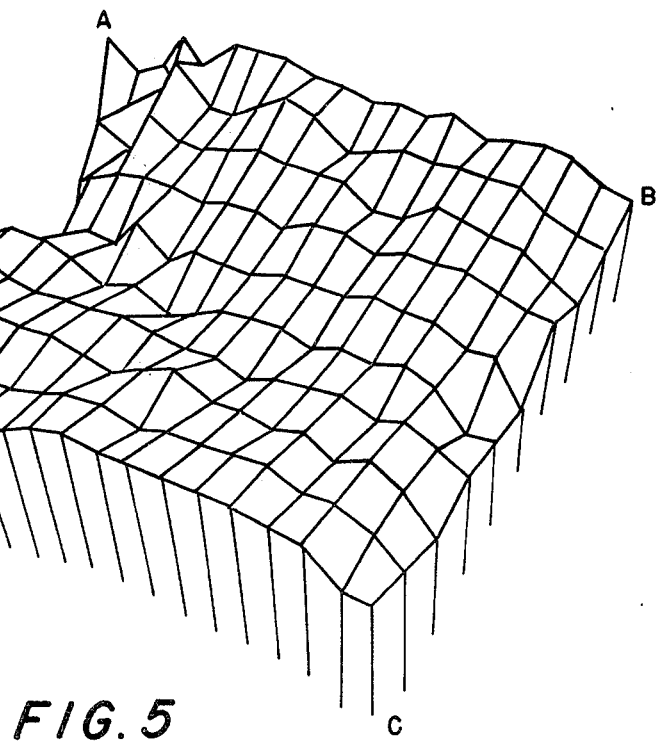
FIG. 5

METHOD AND APPARATUS FOR MEASURING VARIATIONS IN COMPOSITION IN BINARY AND TERNARY SEMICONDUCTORS UTILIZING ELECTROLYTE ELECTROREFLECTANCE

The invention herein described was made in the course of or under a contract, or subcontract thereunder, with the United States Air Force.

This invention relates to an apparatus and method for measuring the variations in composition across the surface of binary and ternary alloy semiconductors utilizing electrolyte electroreflectance (EER), and more particularly to an apparatus and method which are non-destructive and can readily be employed under atmospheric conditions at room temperature.

Electrolyte electroreflectance techniques for measuring semiconductor composition are well-known in the art. The general technique has been described, for example, by Shaklee et al, Electroreflectance at a Semiconductor-Electrolyte Interface, Physical Review Letters, Volume 15, Number 23, Dec. 6, 1965, page 883, and Moritani et al, Electroreflectance Study of $Cd_xHg_{1-x}Te$, Journal of the Physical Society of Japan, Volume 34, Number 1, January, 1973, page 79. But EER techniques have been used in the prior art only in connection with gross measurements; a single determination is made for an entire sample as to its composition. It is very important, however, to be able to determine the spatial composition of a semiconductor material, that is, the chemical composition throughout the surface of the material as it varies in increments in the order of fractions of a millimeter. Such knowledge is useful in the selection of crystals for detector arrays, solid state lasers and electronic devices. Knowledge of the composition variations is also useful in providing feedback for the adjustment of crystal growth parameters, when crystals are grown either in bulk form or epitaxial layers. In the prior art, variations in composition across the surface of an alloy semiconductor have been determined by resort to expensive and cumbersome techniques, such as microprobe and luminescence techniques.

It is a general object of our invention to utilize relatively simple and low-cost EER techniques for measuring composition variations on the surface of alloy semiconductors.

It is well-known that the energies of features in the optical spectra of semiconducting alloys of the binary $A_{1-x}B_x$ (e.g., $Ge_{1-x}Si_x$, etc.) or ternary $A_{1-x}B_xC$ (e.g., $Hg_{1-x}Cd_xTe$, $Ga_{1-x}Al_xAs$, $InAs_{1-x}Sb_x$, $Pb_{1-x}Sn_xTe$, etc.) types depend on composition, x, in a continuous manner. The basic EER technique, as used to measure the gross composition of an alloy semiconductor, entails irradiating the surface of the sample and measuring the intensity of the reflected radiation. The sample is held fixed in a liquid electrolyte. A platinum electrode is held fixed in the electrolyte, and a potential is applied between the sample and the electrode. This arrangement results in a strong electric field at the surface of the semiconductor. A xenon arc is usually used as the light source, the wavelength being varied by passing the output of the source through a monochromator. The intensity of the reflected light depends upon many parameters, including wavelength, electric field and sample characteristics (such as temperature, pressure and stress). But as the wavelength is varied, the intensity of the reflected light exhibits peaks which are unique to each composition. By observing the wavelengths for which the peaks are obtained, the sample composition may be determined.

Prior to the development of modulation spectroscopy, one problem faced by workers in the field was that it was difficult to observe sharp peaks in the optical response of the material as the wavelength was varied. A major advance in the art was made when a modulating parameter, such as an A.C. electric field, was applied to the sample thus suppressing the featureless background and producing sharp spectral features. In EER, a D.C. field is also applied to bring the sample into the blocking region thus allowing the full A.C. field to be applied to the narrow space charge region near the surface. By measuring only the A.C. component in the reflected light, pronounced peaks can be observed as the wavelength of the input light is swept across the visible portion of the spectrum. (Actually, the wavelength may be swept slightly beyond both ends of the visible portion of the spectrum.) A basic experimental system, as well as the effect of the A.C. modulation, is described in Cardona et al, Electroreflectance at a Semiconductor-Electrolyte Interface, Physical Review, Volume 154, Number 3, Feb. 15, 1967, Page 696 (see especially page 703). Reference plots have been published by many investigators which depict peak changes in reflectance as a function of wavelength for materials of known composition. This data has in turn been replotted as peak transition energy (corresponding to respective wavelengths) as a function of composition. Thus for any binary or ternary alloy semiconductor, once it is determined which particular wavelength of a selected optical feature results in a peak measurement, the plot can be consulted to determine the precise composition of the bulk material.

We have discovered that by measuring changes in energy or wavelength of a particular optical feature using a small scanned light spot, the variations in composition x can be determined across the surface of an alloy semiconductor material. EER is particularly advantageous as a measurement technique since it yields a sharp optical spectrum at room temperature, can be performed on a free surface (i.e., nothing need be deposited on the sample surface to apply the electric field), and hence is non-destructive.

In accordance with the principles of our invention, the sample of interest is secured to an X-Y stage; stepper motors move the sample in two dimensions in the electrolyte across the path of the impinging radiation. For each position of the sample, the wavelength of the impinging radiation is swept through its range and the wavelength which results in a peak measurement for a selected optical feature is noted. The sample is moved a distance in the order of fractions of a millimeter between measurements. The peak-producing wavelengths are converted into compositional changes (around a nominal composition) which can then be plotted on a contour map to provide a visual presentation of compositional homogeneity.

Further objects, features and advantages of our invention will become apparent upon consideration of the following detailed description in conjunction with the drawing, in which:

FIG. 4 is a typical contour map generated from the measurement results on a particular $Hg_{1-x}Cd_xTe$ sample having a nominal value of x = 0.21; and FIG. 5 is a perspective drawing of the three-dimensional representation of the contour map of FIG. 4.

Figure 1:
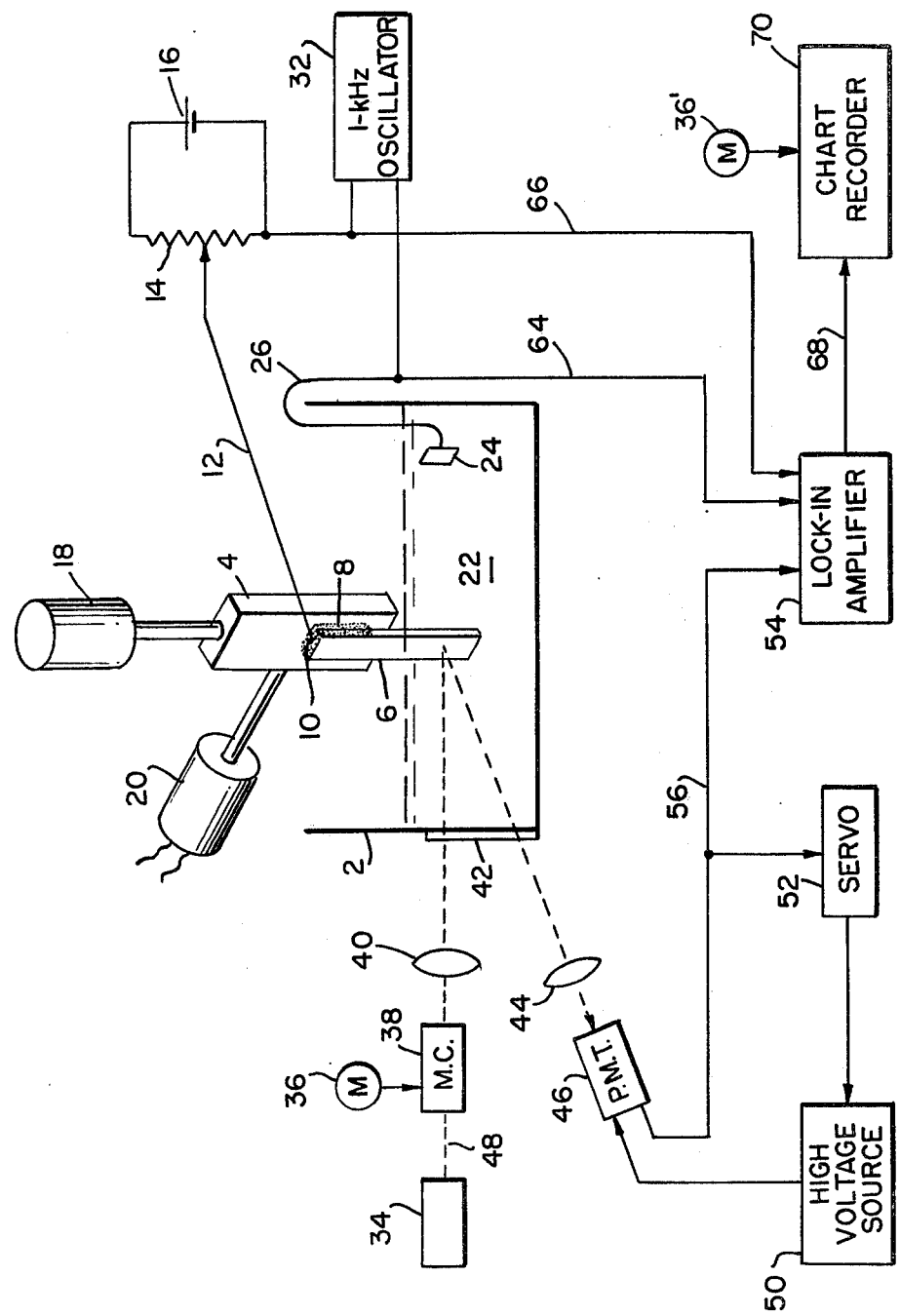
FIG. 1 depicts an apparatus for determining topographical variations in composition, x, using electrolyte electroreflectance.

After suitable preparation of the surface of the semiconductor sample 6 of FIG. 1 (the preparation of the sample will be described below), wire 12 is soldered at 10 to one edge of the sample. The sample is then mounted on glass slide 4 with paraffin wax 8 applied to insulate all but the front surface from the electrolyte employed in the method. The slide is part of X-Y stage 4 (shown symbolically only) which is movable with a precision of 0.01 mm in both directions by stepper motors 18 and 20. The sample is held immersed in a container 2 containing the electrolyte 22 and a platinum electrode 24. (Different electrolytes are used for various materials as will be described below; an electrolyte is chosen which avoids electrochemical interaction with the sample surface, as is known in the art.) The paraffin wax is used to avoid sharp electric field concentrations at the edges of the sample being operated upon. Although not shown in the drawing, container 2, lenses 40 and 44, photomultiplier tube 46, and motors 18 and 20 are all contained in a "light-tight" enclosure.

Light from xenon arc lamp 34 passes through monochromator 38 and is focused onto the sample with a spot size of approximately 100 microns by means of a high quality f/1.2 50 mm camera lens. The spot size can be verified by passing the beam through a 100-micron slit without any loss of intensity. The reflected light is collected by a large lens 44 and focused onto photomultiplier tube 46. Container 2 is provided with a quartz window which is highly transmissive for the short wavelengths of the impinging and reflected radiation (the axis of which is shown by the numeral 48).

Wire 12 is connected to the tap of potentiometer 14, across which D.C. power supply 16 is connected. The lower end of the potentiometer is connected to one output terminal of 1-kHz oscillator 32, the other output terminal of which is connected to electrode 24. The D.C. bias is chosen to bring the electrolyte/sample system into the blocking regime. The light detected by the photomultiplier tube contains two signals, a D.C. signal proportional to the average reflectivity R and an A.C. signal which is proportional to the modulated reflectivity $\Delta R$. The D.C. output from the photomultiplier tube is applied to a servo 52 which adjusts the output of high voltage source 50 such that the D.C. output of the photomultiplier tube is held constant. Under these conditions the A.C. output of the photomultiplier tube is normalized; the electroreflectance signal on conductor 56 is $\Delta R/R$, as is known in the art. This procedure automatically corrects for any fluctuations in the intensity of the reflected light due to variations in the surface of the material or changes in incident light intensity.

The A.C. modulating signal is applied over conductors 64, 65 to lock-in amplifier 54. The signal controls the amplifier to respond to the A.C. component only in the signal output of the photomultiplier tube on conductor 56. As is known in the art, the lock-in amplifier includes a phase-sensitive detector which allows the signal of interest on conductor 56 to be distinguished from background noise.

Figure 2:
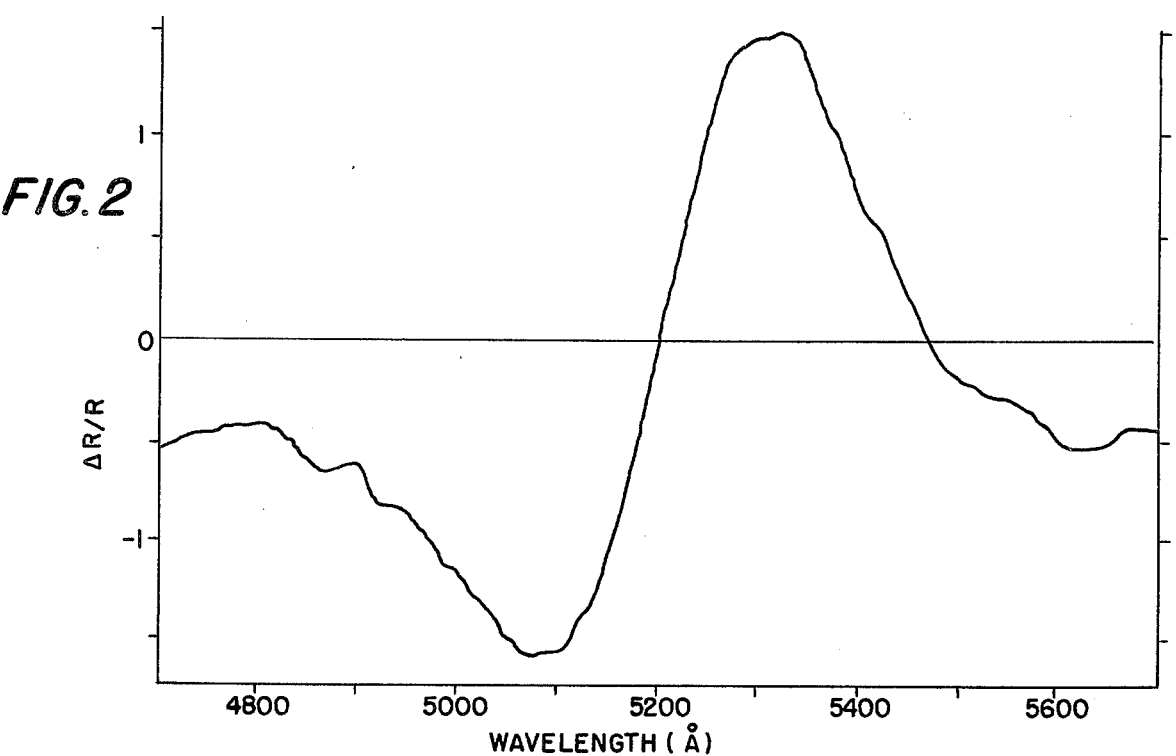
FIG. 2 depicts a typical EER signal $\Delta R/R$ in the region of the $E_1$ optical structure for a $Hg_{1-x}Cd_xTe$ sample with a nominal composition of $x=0.21$.

The resulting $\Delta R/R$ signal on conductor 68 is applied to the input of strip chart recorder 70. The chart is moved by motor 36' at a rate which tracks the sweeping of monochromator 38 by motor 36. (The two motors may be driven by the same synchronous source. Thus every trace on the chart consists of a signal $\Delta R/R$ as a function of wavelength. Although the X-Y position of the sample for each trace may be written on the trace by hand, it is also possible to automate the equipment such that the stepper motor positions are recorded on the strip chart prior to each trace being taken. The important thing is that the strip chart indicate, for each sample position (i.e., for each irradiated incremental area of the sample), the wavelength which results in a peak response. FIG. 2 depicts a typical trace generated by the chart recorder.

Figure 3:
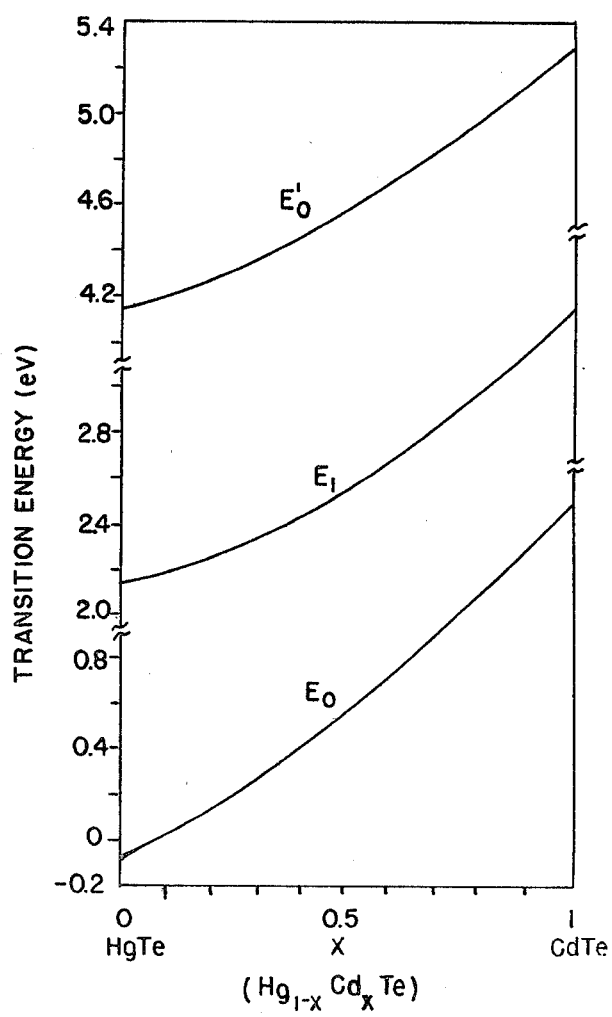
FIG. 3 depicts variations of the $E_0$, $E_1$ and $E_0'$ optical structure with composition x for the same material, the plots being based partially on data contained in the above-identified Moritani et al article.

It is important to select a proper optical structure for the measurements. FIG. 3 depicts known data for the composition $Hg_{1-x}Cd_xTe$, as x varies between 0 and 1; the left side of the horizontal axis (x=0) represents HgTe and the right side (x=1) represents CdTe. Each curve represents a different optical structure, as is known in the art, and depicts the peak transition energy for each composition value. For example, suppose that the $E_1$ optical structure is being investigated. The wavelength is swept through a range corresponding to transition energies in the range 2.1-3.3 electron volts at each sample position. If a $\Delta R/R$ peak corresponds, for example, to a transition energy of 2.4 electron volts, it can be determined that the incremental area being irradiated has a value of x=0.46.

The optical structure selected for any material (the optical structure determining the sweep range) should be one which provides an observable slope in the plot corresponding to that of FIG. 3. (If the plot is horizontal over a range of compositions of interest, then there is no unique value of x corresponding to the wavelength which results in a peak signal.)

Spectra in the vicinity of the most suitable optical feature are taken with the light spot focused onto one portion of the sample. The sample is then moved by means of the X-Y stage and spectra taken in the new position. Step sizes are typically 0.2 mm in the horizontal (x) direction and 0.4 mm along the vertical (Y) direction. After the shifts in energy of the spectra are correlated with the known compositional dependence of that particular feature in order to evaluate the change in composition $\Delta x$ from the nominal value of x for the overall sample, the information may be processed (e.g., by a Tektronix 4051 Basic Graphic System) to produce contour maps and three-dimensional projections of the contours of the topographical features of the variations in stoichiometry, as will be described.

In semiconductors which lack inversion symmetry it is possible to have an electro-optic or piezo-electric effect, i.e., an optical spectra feature may be dependent on the applied electric field. Spectra for the various samples to be described below were taken at different electric field (D.C. and A.C.) conditions and it was found that there was no observable shift in the spectral position of the optical structure, that is, the $\Delta R/R$ peaks occurred at the same wavelengths independent of the electric field.

The preferred spot size of the incident light is about 100 microns, although spot sizes up to 200 microns in diameter may be used. For adequate resolution, the step size should be less than five times the spot size in both directions. The thickness of the samples are unimportant, as are their linear dimensions, although typical sample sizes are 1.5×1 mm (FIG. 1 is not drawn to scale). The wavelength of the impinging light can vary across the entire visible spectrum and even slightly beyond both ends; the sweep range selected for any sample, of course, depends on the optical structure being investigated. A xenon arc and monochromator are the preferred light source; the light output exhibits a minimum of noise.

In a first use of the equipment, an unannealed $Hg_{1-x}Cd_xTe$ sample was investigated. The surface of the sample was prepared by mechanically polishing it with $0.5\mu$ and $0.03\mu$ alumina powder and then etching for about one minute in a 1:10 solution of $Br_2$ in anhydrous methanol. This preparation was necessary to eliminate surface damage which resulted from cutting the sample with a saw. The best electrolyte known for this material is a solution of 1 part conc. $HNO_3$ to 5,000 parts of methanol, by volume. The reason for using nitric acid is that any electrochemical reaction taking place at the surface of the sample is likely to produce soluble nitrates which would not form an opaque film on the surface. The nominal value of x was first deduced from density measurements, and was found to be 0.20.

In $Hg_{1-x}Cd_xTe$ the most advantageous optical feature for the subject purpose is the $E_1$ structure since it gives the largest EER signal and is in the 2–3 eV range for which all standard components which may be used in the system (e.g., photomultiplier tube, etc.) generally have a good response characteristic. FIG. 2 is a plot of the EER signal $\Delta R/R$ at a particular sample location as a function of wavelength in the region of the $E_1$ optical structure. Shown in FIG. 3 is the variation of the $E_1$ optical structure with composition x as determined from published EER measurements by Moritani et al. The shifts in the energy of the spectra at all locations on the sample surface were correlated with the known composition dependence on the $E_1$ peak in order to evaluate the changes in composition $\Delta x$ from the nominal value. (From the data of FIG. 3 it is seen that in the range of $\Delta x$ around the nominal value of the selected sample, the slope of the $E_1$ peak as a function of x is such that a change of 0.01 in x would correspond to a shift of about 7.5 meV in energy, or about 15 Å in wavelength, thus making the $E_1$ optical structure a good one for investigatory purposes.)

Shown in FIG. 4 is a contour map of the variations in composition $\Delta x$ of the sample. The lowest measured value of composition was found to be $x=0.21$, and for regions having this composition $\Delta x=0.00$. The contours are at intervals of $\Delta x=0.005$. Although changes in x as small as $\Delta x=0.002$ can be detected, for the sake of clarity contours are plotted in units of $\Delta x=0.005$. The corners of the contour map are labelled ABCD.

The contour map can be plotted by hand, or a computer with a graphics facility can be used for this purpose. The numbers 1–5 along the contour lines represent $\Delta x$ values in increments of 0.005. The circled letter A in the drawing represents a region of "uniform" compositional homogeneity — all spots having a $\Delta x$ value between 0.00 and 0.005 are included in this region (the actual values of x for the material in this region thus ranging from 0.210 to 0.215). Some of the other regions of "uniform" compositional homogeneity (that is, uniform over a range $\Delta x=0.005$ in this case) are also labelled with circled letters. In region B, $\Delta x$ varies between 0.005 and 0.010; in region C, $\Delta x$ varies between 0.010 and 0.015; in region D, $\Delta x$ varies between 0.015 and 0.020; and in region E, $\Delta x$ varies between 0.020 and 0.025. These are the main regions of interest although there are others of uniform compositional homogeneity as seen in the plot.

FIG. 5 is a three-dimensional projection of the contours of FIG. 4, a drawing which can be generated with standard computer software, and simply represents the measured data in a different form. It can be seen that the sample is quite uniform in the upper right-hand corner, with a major central depression along edge AD.

When testing samples of $Ga_{1-x}Al_xAs$, the samples were utilized without polishing or etching the material. These particular samples were grown by liquid phase epitaxy, had good optical surfaces, and were approximately $2\mu$ thick. (Nominal values of x were deduced from the phase diagram for growth conditions.) The electrolyte used was a 1:4 solution of glycerol in distilled water. For $Ga_{1-x}Al_xAs$, the most convenient optical structure is the $E_0$ feature which corresponds to the direct band gap at $k = 0$.

When testing one $Ga_{1-x}Al_xAs$ sample, it was found that in one region there was a change in phase of the EER signal ($\Delta R/R$) relative to the rest of the sample. This indicates that in this region the band bending is of opposite type in relation to the rest of the sample.

The sample surfaces of single crystal $InAs_xSb_{1-x}$ alloys were polished and etched as were the $Hg_{1-x}Cd_xTe$ samples. The electrolyte used was 1:4 solution of glycerol in water. Nominal values of x were deduced from lattice constants measured by X-ray diffraction.

For this alloy system the most convenient optical structure for the subject purposes is the $E_0'$ feature; in the regions of low x (the samples had low x values), only the $E_0'$ structure exhibits a substantial composition dependence.

Samples of single-crystal $Pb_{1-x}Sn_xTe$ were also tested. The surfaces of these samples were polished as were the $Hg_{1-x}Cd_xTe$ and $InAs_{1-x}Sb_x$ materials. The etchant used was a 25:1 ratio (by weight) of NaOH and $I_2$ in 10 ml of distilled water. The electrolyte used was 1 gram of tetraethyl ammonium perchlorate in 200 cc of propylene carbonate. Nominal composition values were deduced from lattice constants measured by X-ray diffraction.

For $Pb_{1-x}Sn_xTe$, the most advantageous EER structure is the $E_3$ feature. However, in contrast to the other semiconducting alloys which were investigated, the composition dependence of the $E_3$ structure has not yet been determined. But from two available $Pb_{1-x}Sn_xTe$ samples with nominal x values of 0.18 and 0.22, plus a sample of PbTe, it was possible to make a reasonable estimate of the variation of the energy of the $E_3$ peak with x. The $E_3$ structure occurs around 3 eV and is broad compared to the EER peaks utilized for the other materials discussed above.

Although several ternary materials ($Hg_{1-x}Cd_xTe$, $Ga_{1-x}Al_xAs$, $InAs_{1-x}Sb_x$, $Pb_{1-x}Sn_xTe$) have been investigated and discussed above, the application of the technique of our invention to binary semiconductors is evident. The method is non-destructive and can readily be employed at room temperature under atmospheric conditions. The equipment required is relatively inexpensive and can be readily assembled. The technique is sensitive enough to determine changes of composition of about 1% with a spatial resolution of under $200\mu$. In the illustrative embodiment of the invention, the spot size was 100μ; the spatial resolution can be improved by a factor of two with the use of high-quality optics although this may not be necessary since the results thus far have demonstrated that the variations in x have about the same dimensions as a 100μ light spot.

The incremental steps of the X-Y stage, i.e., the distances between the spots in the array of spots for which measurements are taken, should be commensurate with the desired resolution of the compositional homogeneity to be determined. Preferably, the distances between spots should be less than five times the spot size.

The technique of the invention allows actual values of x to be recorded, for example, on a contour map; by correlating the wavelength at which a peak in the EER signal occurs with a value of x (by use, for example, of reference data such as that of FIG. 2), the actual composition of the material across its surface can be determined. But if all that is desired is an indication of the degree of compositional homogeneity without actual values of x, then it is not necessary to translate a wavelength value to a value of x. Each region of the plot of FIG. 4, besides representing values of x within a narrow range, also represents a corresponding narrow range of wavelengths which resulted in EER peaks. A contour map of Δλ values may be made without ever determining x values if all that is desired is an indication of the compositional homogeneity of the sample.

The approach of our invention has several advantages over the microprobe technique. The microprobe, while it does yield a surface analysis with a resolution of 1μ, is not entirely satisfactory. This is due to the fact that a nominal composition obtained by a microprobe analysis is no guarantee that the B atoms, for example, in the alloy $A_{1-x}B_xC$, all occupy their normal sites in the lattice and therefore that one can reasonably deduce from the measured composition a value of the optical band gap. In contrast, our method determines an effective composition correlated to the optical band gap. Furthermore, the equipment needed to utilize the EER technique is a factor of 10 less expensive than microprobe apparatus and the scanned spot size is more consistent with array dimensions.

The EER technique has a number of advantages over luminescence techniques, including the fact that it can be used for small band gap materials. Although luminescence methods can tell a great deal about the material, considerable supporting information must be available in order to make use of luminescence data. As an example, a great deal of the luminescence of III-V compounds, particularly at temperatures below 300° K., involves donors, acceptors and bound excitons. Thus conclusions about the band structure can be reached only after these impurity effects are properly considered. EER, on the other hand, gives direct information about the intrinsic band gap irrespective of the nature of the impurity content. Furthermore, it can be readily utilized at room temperature.

Although the invention has been described with reference to a particular embodiment, it is to be understood that this embodiment is merely illustrative of the application of the principles of the invention. For example, instead of moving the sample, it is possible to maintain it stationary and instead to focus the light spot by means of a scanning system. Thus, numerous modifications may be made in the illustrative embodiment of the invention and other arrangements may be devised without departing from the spirit and scope of the invention.

What we claim is:

1. A method of determining the compositional homogeneity at the surface of an alloy semiconductor comprising the steps of:
    (a) immersing the alloy semiconductor in an electrolyte and applying an electric field having D.C. and A.C. components therein to the surface of interest,
    (b) directing light radiation having a swept wavelength toward a spot on said surface, and measuring the light reflected from said spot to determine the wavelength at which a peak occurs in a selected optical structure,
    (c) determining the composition of said spot from reference data indicative of the wavelength at which peak reflectance is achieved as a function of composition,
    (d) repeating steps (b) and (c) for an array of spots on said surface spaced from one another at distances commensurate with the desired resolution of the compositional homogeneity to be determined, and
    (e) recording regions of uniform compositional homogeneity corresponding to the spot compositions determined in successive performances of step (c).

2. A method in accordance with claim 1 wherein the size of said spot is less than 200 microns in diameter.

3. A method in accordance with claim 2 wherein the distances between spots on said surface are less than five times the spot size.

4. A method of determining the compositional homogeneity at the surface of an alloy semiconductor comprising the steps of:
    (a) immersing the alloy semiconductor in an electrolyte and applying an electric field having D.C. and A.C. components therein to the surface of interest,
    (b) directing light radiation having a swept wavelength toward a spot on said surface, and measuring the light reflected from said spot to determine the wavelength at which a peak occurs in a selected optical structure,
    (c) repeating step (b) for an array of spots on said surface spaced from one another at distances commensurate with the desired resolution of the compositional homogeneity to be determined, and
    (d) recording each region of uniform compositional homogeneity having spots therein at which peak reflectance occurred in step (b) at wavelengths within a narrow range corresponding to said uniform region.

5. A method in accordance with claim 4 wherein the recording made in step (d) is in the form of a contour map.

6. A method in accordance with claim 5 wherein the size of said spot is less than 200 microns in diameter.

7. A method in accordance with claim 6 wherein the distances between spots on said surface are less than five times the spot size.

8. Apparatus for determining surface composition characteristics of an alloy semiconductor sample comprising an electrolyte electroreflectance system for directing light radiation having a swept wavelength through a range of wavelengths associated with a selected optical structure toward a spot on the surface of said sample and measuring the light reflected therefrom as a function of wavelength, said system including an electrolyte in which said sample is immersed and means for applying an electric field having D.C. and A.C. components therein to the surface of said sample, means for moving relative to each other in discrete steps said sample and said light radiation such that said light impinges on successive discrete spots on said surface, and means for recording the measured light reflected from each discrete spot on said surface as a function of wavelength.

9. Apparatus in accordance with claim 8 wherein the size of the spot on which said light radiation impinges has a diameter smaller than 200 microns.

10. Apparatus in accordance with claim 9 wherein said moving means controls said discrete spots to be separated from each other by distances smaller than five times the spot size.

* * * * *